(12) United States Patent
Venturi

(10) Patent No.: US 10,470,922 B1
(45) Date of Patent: Nov. 12, 2019

(54) BLOOD FLOW RESTRICTING HEADWEAR

(71) Applicant: Mark Louis Venturi, Washington, DC (US)

(72) Inventor: Mark Louis Venturi, Washington, DC (US)

(*) Notice: Subject to any disclaimer, the term of this patent is extended or adjusted under 35 U.S.C. 154(b) by 0 days.

(21) Appl. No.: 15/978,917

(22) Filed: May 14, 2018

(51) Int. Cl.
*A61F 7/00* (2006.01)

(52) U.S. Cl.
CPC ...... *A61F 7/007* (2013.01); *A61F 2007/0007* (2013.01); *A61F 2007/0008* (2013.01); *A61F 2007/0075* (2013.01); *A61F 2007/0091* (2013.01)

(58) Field of Classification Search
CPC .............. A61F 7/007; A61F 2007/0007; A61F 2007/0008; A61F 2007/0075; A61F 2007/0091; A61F 2007/0093; A61F 2007/0095; A61F 2007/0096; A61F 2007/0219; A61F 2007/0287; A61F 2007/00; A61F 2007/0054; A61F 2007/0055; A61F 2007/0057; A61F 2007/0059
USPC ................................................ 607/110, 104
See application file for complete search history.

(56) References Cited

U.S. PATENT DOCUMENTS

| | | | |
|---|---|---|---|
| 4,172,495 A | 10/1979 | Zebuhr et al. | |
| 4,354,496 A | 10/1982 | Andersen | |
| 4,425,916 A | 1/1984 | Bowen | |
| 4,470,263 A | 9/1984 | Lehovec et al. | |
| 4,566,455 A | 1/1986 | Kramer | |
| 4,572,188 A | 2/1986 | Augustine et al. | |
| 4,915,108 A | 4/1990 | Sun | |
| 5,172,689 A * | 12/1992 | Wright | A61F 7/10 602/2 |
| 5,342,411 A | 8/1994 | Maxted et al. | |
| 5,603,728 A | 2/1997 | Pachys | |
| 5,755,756 A | 5/1998 | Freedman, Jr. et al. | |

(Continued)

FOREIGN PATENT DOCUMENTS

| | | |
|---|---|---|
| JP | 2011000342 A | 1/2011 |
| RU | 2341737 C2 | 6/2008 |
| WO | 2014143853 A2 | 9/2014 |

OTHER PUBLICATIONS

International Search Report for PCT/US2019/031708 dated Aug. 22, 2019.

*Primary Examiner* — Linda C Dvorak
*Assistant Examiner* — Christine A Dedoulis
(74) *Attorney, Agent, or Firm* — PK Patent Law

(57) ABSTRACT

A blood flow restricting apparatus is provided. The blood flow restricting apparatus can include a frame element configured to be securable to a user's head. At least one cooling pad can be operatively arranged with the adjustable frame element and configured to be arranged over a defined anatomic location including at least one of a pair of supratrochlear arteries, a pair of supraorbital arteries, a pair of temporal arteries, and a pair of occipital arteries of the user's head when the frame element is secured to the user's head. A pressurizing mechanism can be operatively arranged with the at least one cooling pad and capable of pressing the at least one cooling pad against the defined anatomic location to restrict blood flow to each of the targeted arteries while simultaneously cooling the defined anatomic location to induce hypothermic induced vasoconstriction.

22 Claims, 2 Drawing Sheets

(56) References Cited

U.S. PATENT DOCUMENTS

| | | |
|---|---|---|
| 5,848,981 A | 12/1998 | Herbranson |
| 5,871,526 A | 2/1999 | Gibbs et al. |
| 6,125,636 A | 10/2000 | Taylor et al. |
| 6,156,059 A | 12/2000 | Olofsson |
| 6,277,143 B1 * | 8/2001 | Klatz ................. A61F 7/00 607/104 |
| 6,962,600 B2 | 11/2005 | Lennox et al. |
| 6,986,783 B2 | 1/2006 | Gunn et al. |
| 7,008,445 B2 | 3/2006 | Lennox |
| 7,022,093 B2 | 4/2006 | Smith et al. |
| 7,052,509 B2 | 5/2006 | Lennox et al. |
| 7,087,075 B2 | 8/2006 | Briscoe et al. |
| 7,156,867 B2 | 1/2007 | Lennox |
| 7,179,279 B2 | 2/2007 | Radons et al. |
| 7,507,250 B2 | 3/2009 | Lennox |
| 7,571,615 B1 | 8/2009 | Bikes |
| 7,621,945 B2 | 11/2009 | Lennox et al. |
| 7,744,640 B1 * | 6/2010 | Faries, Jr. ........... A61F 13/00 607/108 |
| 8,087,254 B2 | 1/2012 | Arnold |
| 8,454,671 B2 | 6/2013 | Lennox et al. |
| 8,491,505 B2 | 7/2013 | Yang |
| 8,499,365 B1 | 8/2013 | Hill |
| 8,529,613 B2 | 9/2013 | Radziunas et al. |
| 8,603,151 B2 | 12/2013 | Latham |
| 2002/0091431 A1 | 7/2002 | Gunn et al. |
| 2005/0193742 A1 | 9/2005 | Arnold |
| 2009/0054958 A1 | 2/2009 | Nofzinger |
| 2010/0186436 A1 | 7/2010 | Stormby |
| 2010/0198322 A1 | 8/2010 | Joseph et al. |
| 2011/0078845 A1 | 4/2011 | McKinney |
| 2012/0041526 A1 | 2/2012 | Stormby |
| 2013/0138185 A1 | 5/2013 | Paxman et al. |
| 2014/0046410 A1 | 2/2014 | Wyatt |
| 2014/0236271 A1 | 8/2014 | Fronda et al. |
| 2015/0173445 A1 | 6/2015 | Gordon et al. |
| 2015/0238354 A1 | 8/2015 | Rajguru et al. |
| 2016/0143771 A1 | 5/2016 | Swyer et al. |
| 2016/0317348 A1 * | 11/2016 | Banker ............... A61H 9/0078 |
| 2018/0199879 A1 * | 7/2018 | Kanistros ............ A61B 5/448 |

* cited by examiner

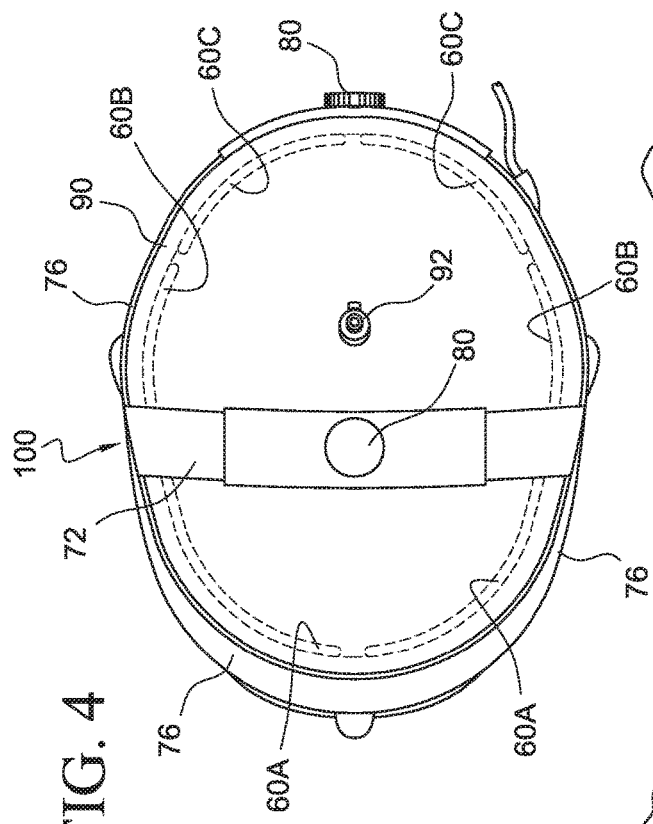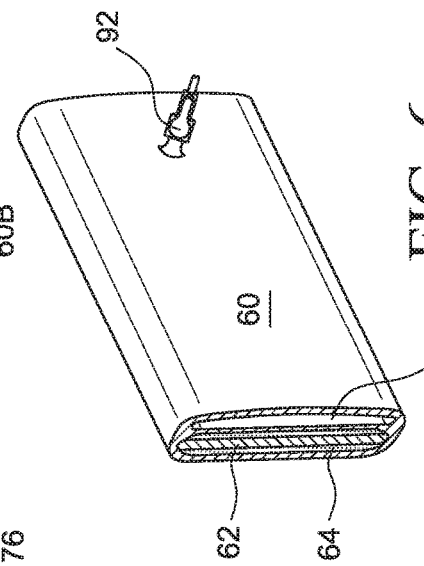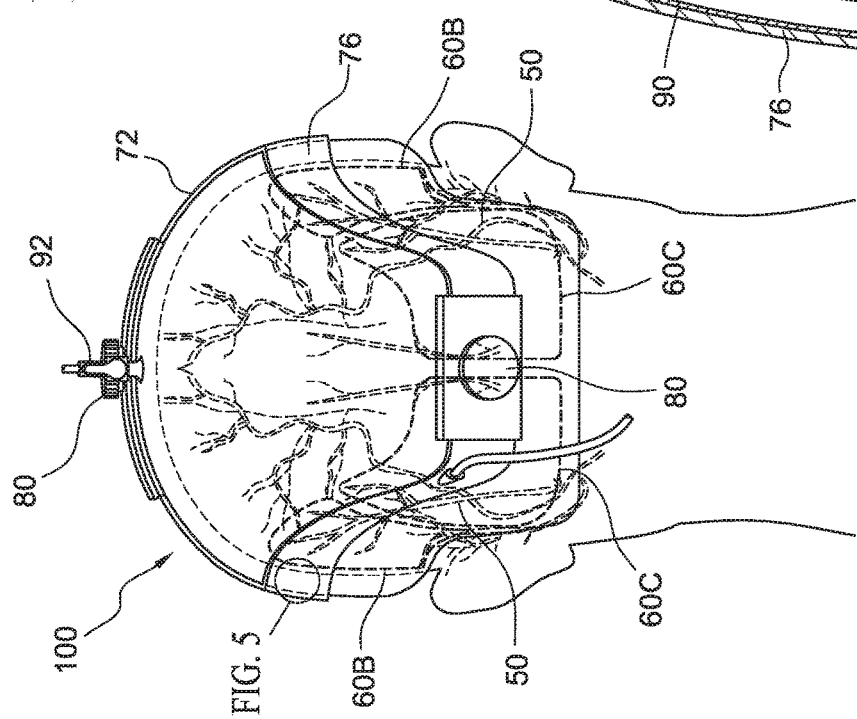

BLOOD FLOW RESTRICTING HEADWEAR

FIELD OF THE INVENTION

The present teachings relate to headwear for restricting arterial blood flow to a person's scalp to prevent hair loss resulting from agents in the blood such as those from chemotherapy treatment.

BACKGROUND OF THE INVENTION

Headwear is known for removing heat from a person's scalp in order to prevent hair loss.

One known type of scalp cooling headwear is a stand-alone device that is first cooled to a required temperature and then placed on the person's head. However, this type of cooling headwear needs to be continuously replaced as its cooling effectiveness is quickly reduced as heat from the person's head warms up the headwear. This type of scalp cooling headwear is known to have limited or no adjustability thereby limiting efficient cooling of the scalp.

Another known type of scalp cooling headwear includes a cold fluid that is circulated through the headwear. This type of known headwear requires a source of cold fluid and a pump for pumping the cold fluid through the headwear. This type of headwear is oftentimes unsatisfactory in that the headwear doesn't fit sufficiently tightly to the person's head during use with the result that the headwear does not fully restrict blood flow to the scalp or cool the person's scalp as efficiently as it should.

Accordingly, there exists a need for an adjustable helmet or headpiece that can securely fit to a patient's head that simultaneously provides both targeted pressure and cold temperatures to defined anatomic locations to restrict arterial flow to the hair-baring scalp.

SUMMARY OF THE INVENTION

The present teachings provide a blood flow restricting apparatus including a frame element configured to be securable to a user's head. The blood flow restricting apparatus can include at least one cooling pad operatively arranged with the frame element and capable of being placed over at least one of i) corresponding pairs of supratrochlear and supraorbital arteries, ii) a corresponding pair of temporal arteries, and iii) a corresponding pair of occipital arteries of the user's head, each of the at least one cooling pad including a cooling element. At least one bladder can be operatively arranged with the at least one cooling pad and capable of being supplied with a fluid so that the at least one cooling pad is capable of pressing against the at least one of i) the corresponding pairs of supratrochlear and supraorbital arteries, ii) the corresponding pair of temporal arteries, and iii) the corresponding pair of occipital arteries. The at least one cooling pad can be configured to simultaneously cool and restrict blood flow to the at least one of i) the corresponding pairs of supratrochlear and supraorbital arteries, ii) the corresponding pair of temporal arteries, and iii) the corresponding pair of occipital arteries when the frame element is secured to the user's head.

The present teachings also provide another embodiment of a blood flow restricting apparatus including a frame element configured to be securable to a user's head. The blood flow restricting apparatus can include at least one cooling pad operatively arranged with the adjustable frame element and configured to extend over a defined anatomic location including at least one of i) corresponding pairs of supratrochlear and supraorbital arteries, ii) a corresponding pair of temporal arteries, and iii) a corresponding pair of occipital arteries of the user's head when the frame element is secured to the user's head, the at least one cooling pad including a cooling element capable of producing a cooling effect. A pressurizing mechanism can be operatively arranged with the at least one cooling pad and capable of pressing the at least one cooling pad against the defined anatomic location to restrict blood flow to the user's head while simultaneously cooling the defined anatomic location to induce hypothermic induced vasoconstriction.

The present teachings further provide yet another embodiment of a blood flow restricting apparatus including a frame element configured to be adjustably securable to a user's head. The blood flow restricting apparatus can include at least one cooling pad operatively arranged with the adjustable frame element and configured to be extend over each of a pair of supratrochlear arteries, a pair of supraorbital arteries, a pair of temporal arteries, and a pair of occipital arteries of the user's head. The at least one cooling pad can include a cooling element capable of producing a cooling effect. A pressurizing mechanism can be operatively arranged with the at least one cooling pad and configured to press the at least one cooling pad against each of the pair of supratrochlear arteries, the pair of supraorbital arteries, the pair of temporal arteries, and the pair of occipital arteries when the frame element is secured to the user's head. The at least one cooling pad can be configured to simultaneously cool and restrict blood flow to each of the pair of supratrochlear arteries, the pair of supraorbital arteries, the pair of temporal arteries, and the pair of occipital arteries when the frame element is secured to the user's head.

Additional features and advantages of various embodiments will be set forth, in part, in the description that follows, and will, in part, be apparent from the description, or may be learned by the practice of various embodiments. The objectives and other advantages of various embodiments will be realized and attained by means of the elements and combinations particularly pointed out in the description herein.

BRIEF DESCRIPTION OF THE DRAWINGS

FIG. 3 shows a back view of the blood flow restricting apparatus of FIG. 1;

FIG. 4 shows a top view of the blood flow restricting apparatus of FIG. 1;

FIG. 5 shows a cross-sectional detail of a left-side lateral cooling pad of the blood flow restricting apparatus taken at detail-5—of FIG. 3; and FIG. 6 shows a cross-sectional perspective view of a cooling pad of the blood flow restricting apparatus including an integrally formed bladder.

Figures 1, 2:
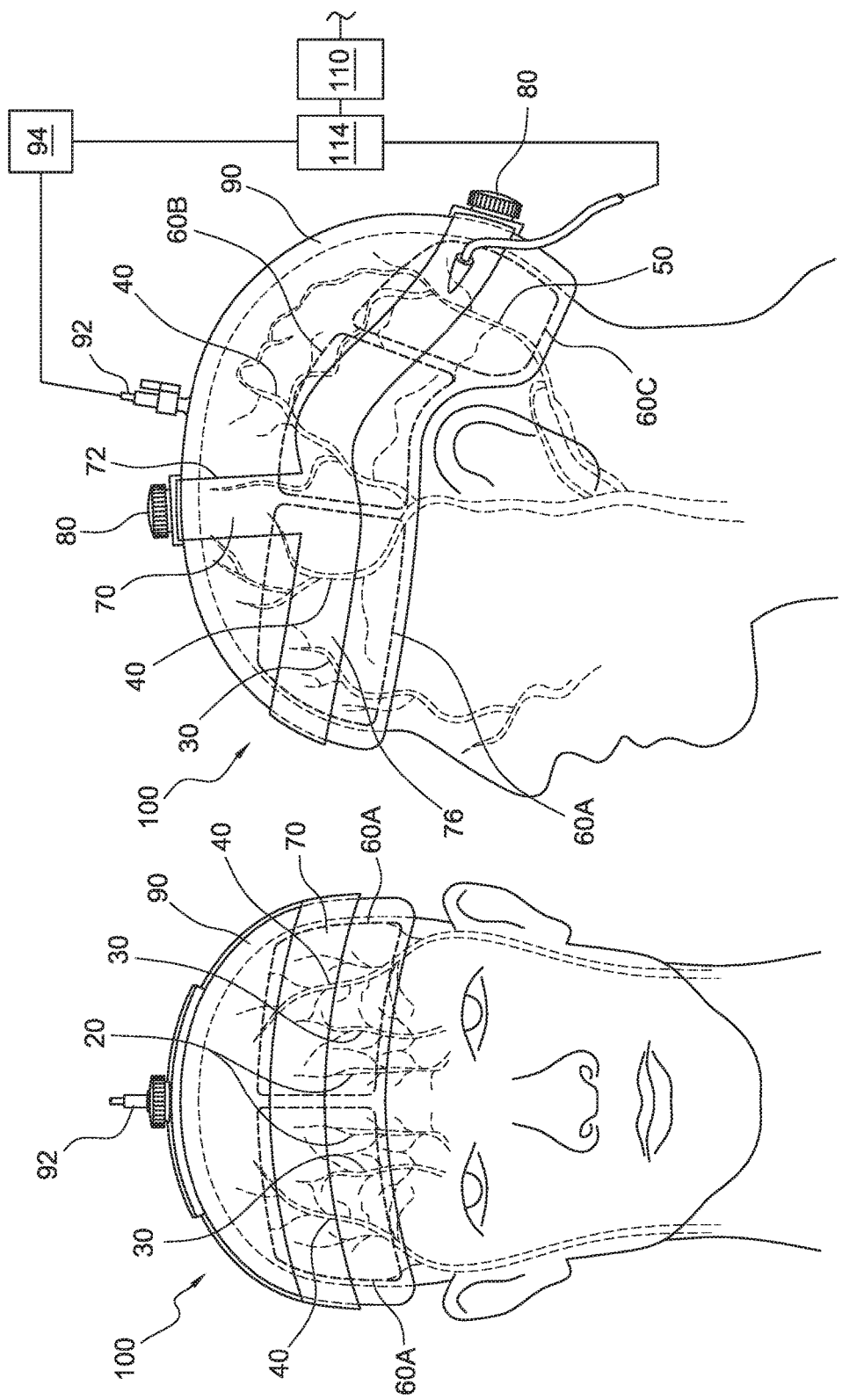
FIG. 1 shows a from view of the blood flow restricting apparatus of the present teachings secured to a head of a patient.
FIG. 2 shows a side view of the blood flow restricting apparatus of FIG. 1.

It is to be understood that both the foregoing general description and the following detailed description are exemplary and explanatory only, and are intended to provide an explanation of various embodiments of the present teachings.

DETAILED DESCRIPTION OF THE PREFERRED EMBODIMENTS

Referring initially to FIGS. 1 to 3, a blood flow restricting apparatus 100 that attaches to a patient's head in accordance with a preferred embodiment of the present teachings is shown. The blood flow restricting apparatus 100 can include one or more cooling pads 60A, 60B, 60C located anteriorly, laterally, and posteriorly of a patient's head that are capable of being selectively or simultaneously pressed against nutrient vessels that supply the scalp with blood. The nutrient vessels targeted by the blood flow restricting apparatus 100 of the present teachings provide the majority of the blood flow to the scalp and include the supratrochlear arteries 20, the supraorbital arteries 30, the temporal arteries 40, and the occipital arteries 50. As will be discussed in more detail below, one or more pumps 94 can be implemented to supply external pressure to force the one or more cooling pads 60A, 60B, 60C against the targeted pairs of arteries 20, 30, 40, 50 on either side of the patient's head.

To further restrict blood flow to the scalp, each of the one or more cooling pads 60A-60C of the blood flow restricting apparatus 100 can include a cooling element such as a thermoelectric cooling element or plate 62, as shown in FIG. 5. The cooling element is capable of producing a cooling effect. For example, when a voltage is applied across the thermoelectric cooling elements 62, the cooling pads 60 can lower the temperature of the scalp in the vicinity of the pair of supratrochlear arteries 20, the pair of supraorbital arteries 30, the pair of temporal arteries 40, and the pair of occipital arteries 50 to achieve hypothermic induced vasoconstriction.

The blood flow restricting apparatus 100 can include a frame element 70 including one or more adjustable straps that can extend about the head of a patient. The frame element 70 can include a top strap 72 having an inner surface positioned to extend over the crown of a patient's head. The ends of the top strap 72 can be rigidly coupled to a circumferential side strap 76. The circumferential side strap 76 can include an inner surface for fitting engagement around the entirety of the patient's head.

FIGS. 1 to 3 show the respective ends of the top strap 72 being rigidly coupled to the circumferential side strap 76. Alternatively, the top strap 72 can be pivotally coupled at its ends to the circumferential side strap 76.

As best shown in FIGS. 2 and 3, the circumferential side strap 76 can be sized and shaped to extend about the forehead, the sides, and the occipital area of the patient's head. The portion of the circumferential side strap 76 that extends about the occipital area can extend angularly downwardly and wrap around or extend along an occipital crest of a wearer and then extend under the occipital crest as shown in FIG. 3. When the circumferential side strap 76 is tightened, the portion of the circumferential strap 76 that extends about the occipital area may rise up and under the occipital crest of the wearer's head to secure the scalp cooling apparatus 100 in place using the natural geometry of the wearer's head.

The circumferential side strap 76 can also include an additional rear strap portion (not shown). The rear strap can be rigidly coupled at its ends to the circumferential side strap 76 and can be positioned to extend around a rear portion of a patient's head. Alternatively, the rear strap can be pivotally coupled at its ends to respective side portions. In such an example, the rear strap 76 can rotate between any range of angles and can be limited in rotation in any manner.

According to various embodiments, the frame element 70 can include a plurality of strap portions rigidly connected to one another, a plurality of strap portions connected to one another by way of pivotal couplings, or can include a combination of rigid and pivotal couplings. A multi-piece circumferential side strap 76 can include a forehead strap portion, an occipital strap portion, a rear strap portion, and the like.

Adjustable tightening members 80 can be coupled to each of the straps of the frame element 70. The adjustable tightening members 80 can allow adjustment of the fit of the scalp cooling apparatus 100 to the head of the patient to minimize any shifting relative to the patient's head and to ensure that each of the one or more cooling pads 60 are properly positioned with respect to the pairs of supratrochlear arteries 20, the pairs of supraorbital arteries 30, the pairs of temporal arteries 40, and the pairs of occipital 50 arteries. The tightening members 80 can be operated by being pushed inward and rotated left or right to adjust the length of the straps to adjust the fit. Alternatively, tightening members 80 can include any mechanism that would allow selective adjustment of the straps as would be appreciated by one of ordinary skill in the art.

Referring to FIGS. 2-4, the one or more cooling pads 60A-60C of the blood flow restricting apparatus 100 are shown operatively coupled with the frame element 70 in a manner such that they can extend over the pairs of supratrochlear arteries 20, the pairs of supraorbital arteries 30, the pairs of temporal arteries 40, and the pairs of occipital arteries 50 when the frame element 70 is secured and adjusted to the specifics of the head of a patient. As shown in detail in FIG. 5, each of the cooling pads 60A-60C can include a thermoelectric cooling element or plate 62, such as a Peltier-type thermoelectric element. A gel 64 can be arranged within each cooling pad 60 and can extend about the thermoelectric element 62. The gel 64 can retain the temperature reduction created by the thermoelectric cooling element 62 and also act to insulate the thermoelectric plate from being in direct contact with the scalp of the patient. Each of the thermoelectric cooling elements 62 can be individually controlled to create a custom spatial cooling profile and/or a time-varying cooling profile.

Moreover, one or more bladders 90 can be situated between the cooling pads 60A-60C and the frame element 70 of the scalp cooling apparatus 100. The bladders 90 can be arranged to extend about the head of the patient in the area of the scalp. As shown in FIGS. 1-4, a unitary bladder 90 can be arranged to extend about the entire scalp area of the patient like a cap. Alternatively, a series of individual bladders 90 can be arranged about the scalp. The one or more bladders 90 can include a nipple 92 which can be used to supply and extract liquid or gaseous fluid to and from the bladders 90 by way of the pump 94. By pressurizing the bladder 90, an external downward pressure can be created by each of the cooling pads 60 by way of the bladder 90 pushing against the frame element 70 thereby restricting arterial blood flow to at least one of the pair of supratrochlear arteries 20, the pair of supraorbital arteries 30, the pair of temporal arteries 40, and the pair of occipital arteries 50.

Alternatively, as shown in FIG. 6, each individual cooling pad 60 can include its own bladder 90 that can be inflated through a nipple 92 to create the downward pressure to restrict arterial blood flow to targeted anatomic locations including arterial flow.

As shown in FIGS. 1-4, one or more cooling pads 60 can be located anteriorly, laterally, and posteriorly with respect to a patient's head in order to target the specific pairs of arteries that supply blood flow to the hair-baring scalp. In the anterior area of the head, one or more cooling pads 60A can be located over corresponding pairs of supratrochlear arteries 20 and supraorbital arteries 30 since these artery pairs are relatively closely situated. In the lateral area of the head, one or more cooling pads 60B can be located over a corresponding pair of temporal arteries 40. In the posterior area of the head, one or more cooling pads 60C can be located over a corresponding pair of occipital arteries 50. According to an embodiment, a single cooling pad 60 can be sized and arranged to extend over each of the corresponding pairs of supratrochlear arteries 20 and supraorbital arteries 30, the corresponding pair of temporal arteries 40, and the corresponding pair of occipital arteries 50. According to another embodiment, a single cooling pad 60 can be sized and arranged to extend over at least one of i) the corresponding pairs of supratrochlear arteries 20 and supraorbital arteries 30, ii) the corresponding pair of temporal arteries 40, and iii) the corresponding pair of occipital arteries 50. The blood flow restricting apparatus 100 of the present teachings thereby allows the targeted and simultaneous compression and cooling of the pairs of supratrochlear, supraorbital, temporal, and occipital arteries by the application of external pressure by one or more cooling pads 60 pressing against the underlying cranium.

The blood flow restricting apparatus 100 can further include a power supply 110 and a processing unit 114 operatively coupled to the one or more cooling pads 60A-60C and to the pump 94 of the scalp cooling apparatus 100. The power supply 110, the processing unit 114, and the pump 94 can be separate and distinct from the portion of the scalp cooling apparatus 100 that secures to the head of a patient.

Initially, the frame element 70 can be arranged about the head of the patient and can then be adjusted to create a secure fit by way of mechanical adjustment via the adjustable tightening members 80. Later, the power supply 110, the processing unit 114, and pump 94 can be operatively coupled to the one or more bladders 90 so that a supply of external pressure can be directed into the bladders 90 to force the cooling pads 60A-60C to squeeze against the targeted pairs of arteries 20, 30, 40, 50. The power supply 110 and the processing unit 114 can also be operatively coupled to the cooling pads 60A-60C to power the thermoelectric cooling.

The power supply 110 can provide a voltage to the cooling plates 62 of each of the cooling pads 60A-60C to effectuate a heat removal rate from the targeted areas of the scalp of the patient. The power supply 110 can also provide a voltage to the pump 94 so that a supply of external pressure can be directed into the one or more bladders 90. The processing unit 114 can monitor process parameters via sensors (not shown) placed proximate to the cooling pads 60A-60C through power lines to adjust the heat removal rate based on the process parameters. The heat transfer rate can be adjusted to maintain constant process parameters. Alternately, the process parameters can vary either spatially or temporally. The processing unit 114 can be in direct electrical communication through dedicated power lines, or alternatively, can be connected via a wireless communication. Alternatively, the processing unit 114 can be preprogrammed to provide a spatially distributed cooling profile and/or a time-varying cooling profile.

The processing unit 114 can also monitor process parameters via sensors (not shown) placed proximate to the one or more bladders 90 to adjust the squeezing force the cooling pads 60A-60C exert against the targeted pairs of arteries 20, 30, 40, 50 based on process parameters.

As a patient places the frame element 70 onto his or her head, the patient will pull the frame element 70 so the front portion of the circumferential side strap 76 slides down the wearer's forehead so that the front cooling pads 60A extend over the pair of supratrochlear arteries 20 and the pair of supraorbital arteries 30. At the same time, the remainder of the frame element 70 can be pushed downwardly until the portion of the circumferential side strap 76 that extends about the occipital area extends angularly downwardly and wraps around or extends along the occipital crest of the patient and under the occipital crest.

At this point, the lateral cooling pads 60B extend over the pair of temporal arteries 40 and the occipital cooling pads 60C extend over the pair of occipital arteries 50. The frame element 70 can then be mechanically adjusted using the adjustable tightening members 80 to achieve a secure fit of the frame element 70 on the patient's head. The bladder (or bladders) 90 can then be selectively pressurized in order to direct a pressure to the targeted pairs of arteries 20, 30, 40, 50 by each of the cooling pads 60A-C to restrict arterial blood flow to the scalp. Simultaneously, power can be selectively provided to the cooling elements 62 of each of the cooling pads 60A-60C to effectuate heat removal from the targeted areas of the scalp of the patient.

The blood flow restricting apparatus 100 of the present teachings thereby combines the simultaneous application of targeted pressure and cooling to one or more of the pairs of supraorbital, supratrochlear, temporal, and occipital arteries of the scalp. The application of multiple modalities of physical forces to the nutrient vessels that supply the scalp with blood severely restricts blood flow at these targeted areas. The scalp cooling apparatus 100 thereby efficiently reduces the delivery of chemotherapeutic drugs to the hair-baring scalp thus reducing the effects of these agents on hair follicles and limiting hair loss during chemotherapy.

Those skilled in the art can appreciate from the foregoing description that the present teachings can be implemented in a variety of forms. Therefore, while these teachings have been described in connection with particular embodiments and examples thereof, the true scope of the present teachings should not be so limited. Various changes and modifications may be made without departing from the scope of the teachings herein.

What is claimed is:

1. A blood flow restricting apparatus for independently restricting blood flow at targeted arterial areas of a scalp comprising:

a frame element configured to be securable to a user's head;

at least one cooling pad operatively arranged with the adjustable frame element and including a cooling element capable of producing a cooling effect, the at least one cooling pad configured to extend over a defined anatomic location including the targeted arterial areas chosen from at least two of i) corresponding pairs of supratrochlear and supraorbital arteries, ii) a corresponding pair of temporal arteries, and iii) a corresponding pair of occipital arteries of the user's head when the frame element is secured to the user's head and lower a temperature of a user's scalp in a vicinity of the targeted arterial areas; and a plurality of independently actuable pressurizing mechanisms extending over the targeted arterial areas whereby each pressurizing mechanism is operatively arranged with the at least one cooling pad and being supported by the frame element over the defined anatomic location, the independently actuable pressurizing mechanisms capable of independently pressing the at least one cooling pad against the defined anatomic location to an extent that blood flow is restricted at the targeted arterial areas while simultaneously cooling the targeted arterial areas to induce hypothermic induced vasoconstriction such that the restricted blood flow reduces a delivery of chemotherapeutic agents to the scalp to limit hair loss.

2. The blood flow restricting apparatus of claim 1, wherein the at least one cooling pad is configured to extend over the defined anatomic location including each of i) the corresponding pairs of supratrochlear and supraorbital arteries, ii) the corresponding pair of temporal arteries, and iii) the corresponding pair of occipital arteries.

3. The blood flow restricting apparatus of claim 1, wherein at least one of the plurality of pressurizing mechanisms is a bladder that is capable of being supplied with a fluid.

4. The blood flow restricting apparatus of claim 3, wherein the bladder is integrally formed with the at least one cooling pad.

5. The blood flow restricting apparatus of claim 3, wherein the bladder is arranged between the frame element and the at least one cooling pad.

6. The blood flow restricting apparatus of claim 1, wherein the frame element includes one or more adjustable straps capable of securing the blood flow restricting apparatus to the head of a user.

7. The blood flow restricting apparatus of claim 1, wherein the cooling element of the at least one cooling pad is a thermoelectric cooling element.

8. The blood flow restricting apparatus of claim 1, further including a processing unit configured to control the cooling element and the plurality of pressurizing mechanisms to simultaneously cool and restrict blood flow at the defined anatomic location.

9. A blood flow restricting apparatus for independently restricting blood flow at targeted arterial areas of a scalp comprising:
  a frame element configured to be securable to a user's head;
  at least one cooling pad operatively arranged with the frame element and including a cooling element capable of producing a cooling effect, the at least one cooling pad configured to extend over the targeted arterial areas defined by at least two arterial areas chosen from i) corresponding pairs of supratrochlear and supraorbital arteries, ii) a corresponding pair of temporal arteries, and iii) a corresponding pair of occipital arteries of the user's head when the frame element is secured to the user's head and lower a temperature of a user's scalp in a vicinity of the targeted arterial areas;
  a plurality of pressurizing mechanisms extending over the targeted arterial areas and each pressurizing mechanism operatively arranged between the frame element and the at least one cooling pad; and
  a processing unit capable of selectively actuating each of the plurality of pressurizing mechanisms thereby creating a downward pressure by the at least one cooling pad by way of the plurality of pressurizing mechanisms pushing against the frame element to selectively restrict blood flow at the targeted arterial areas while simultaneously cooling the targeted arterial areas.

10. The blood flow restricting apparatus of claim 9, wherein the at least one cooling pad is configured to extend over the targeted arterial areas defined by each of i) the corresponding pairs of supratrochlear and supraorbital arteries, ii) the corresponding pair of temporal arteries, and iii) the corresponding pair of occipital arteries.

11. The blood flow restricting apparatus of claim 9, wherein at least one of the plurality of pressurizing mechanisms is a bladder that is capable of being supplied with a fluid.

12. The blood flow restricting apparatus of claim 11, wherein the bladder is integrally formed with the at least one cooling pad.

13. The blood flow restricting apparatus of claim 9, wherein the frame element includes one or more adjustable straps capable of securing the blood flow restricting apparatus to the head of a user.

14. The blood flow restricting apparatus of claim 9, wherein the cooling element of the at least one cooling pad is a thermoelectric cooling element.

15. The blood flow restricting apparatus of claim 14, wherein the thermoelectric cooling element is surrounded by a gel.

16. A blood flow restricting apparatus for restricting blood flow at targeted arterial areas of a scalp comprising:
  a frame element configured to be securable to a user's head;
  a plurality of cooling pads each operatively arranged with the frame element, each cooling pad including a cooling element capable of producing a cooling effect and a pressurizing mechanism arranged between the frame element and the cooling element;
  the plurality of cooling pads with the pressuring mechanisms configured to extend over the targeted arterial areas defined by at least two arterial areas chosen from i) corresponding pairs of supratrochlear and supraorbital arteries, ii) a corresponding pair of temporal arteries, and iii) a corresponding pair of occipital arteries of the user's head when the frame element is secured to the user's head; and
  a processing unit capable of individually actuating each of the pressurizing mechanisms thereby creating a downward pressure by a corresponding cooling pad pushing against the frame element to restrict blood flow at the targeted arterial areas while simultaneously cooling the targeted arterial areas.

17. The blood flow restricting apparatus of claim 16, wherein the at least one cooling pad is configured to extend over the targeted arterial areas defined by each of i) the corresponding pairs of supratrochlear and supraorbital arteries, ii) the corresponding pair of temporal arteries, and iii) the corresponding pair of occipital arteries.

18. The blood flow restricting apparatus of claim 16, wherein at least one of the pressurizing mechanisms is a bladder that is capable of being supplied with a fluid.

19. The blood flow restricting apparatus of claim 18, wherein the bladder is integrally formed with the at least one cooling pad.

20. The blood flow restricting apparatus of claim 16, wherein the frame element includes one or more adjustable straps capable of securing the blood flow restricting apparatus to the head of a user.

21. The blood flow restricting apparatus of claim 16, wherein the cooling element of the at least one cooling pad is a thermoelectric cooling element.

22. The blood flow restricting apparatus of claim 21, wherein the thermoelectric cooling element is surrounded by a gel.

* * * * *